United States Patent [19]
Ho et al.

[11] Patent Number: 5,847,834
[45] Date of Patent: Dec. 8, 1998

[54] EXPANDABLE, CONTINUOUS ILLUMINATION SOURCE FOR A WEB INSPECTION ASSEMBLY AND METHOD

[75] Inventors: Morris D. Ho, Lafayette; Walter I Golz, Oakland, both of Calif.

[73] Assignee: Webview, Inc., Dillon Beach, Calif.

[21] Appl. No.: 927,736

[22] Filed: Sep. 11, 1997

[51] Int. Cl.$^6$ .................................................. G01N 21/89
[52] U.S. Cl. ...................... 356/429; 250/227.3; 430/430
[58] Field of Search .................................... 356/429, 430, 356/431; 250/227.31

[56] References Cited

U.S. PATENT DOCUMENTS

| | | |
|---|---|---|
| 3,574,469 | 4/1971 | Emerson . |
| 3,609,044 | 9/1971 | Murphy . |
| 3,618,063 | 11/1971 | Johnson . |
| 3,693,021 | 9/1972 | Lake, Jr. et al. . |
| 3,734,624 | 5/1973 | Cornelius . |
| 3,778,631 | 12/1973 | Allinger et al. . |
| 3,779,649 | 12/1973 | Bertoya et al. . |
| 3,800,157 | 3/1974 | Nichols . |
| 3,814,520 | 6/1974 | Baker et al. ............................. 356/71 |
| 3,814,943 | 6/1974 | Baker et al. . |
| 3,814,945 | 6/1974 | Allnutt et al. . |
| 3,835,332 | 9/1974 | Bridges . |
| 3,843,890 | 10/1974 | Anthony, Jr. et al. . |
| 3,958,127 | 5/1976 | Faulhaber et al. . |
| 4,004,152 | 1/1977 | Obser et al. . |
| 4,004,153 | 1/1977 | Obser et al. . |
| 4,166,541 | 9/1979 | Smith, Jr. ................................ 209/587 |
| 4,170,419 | 10/1979 | Van Tyne et al. ....................... 356/431 |
| 4,173,441 | 11/1979 | Wolf ........................................ 356/431 |
| 4,232,336 | 11/1980 | Henry . |
| 4,234,135 | 11/1980 | Conner, Jr. . |
| 4,237,539 | 12/1980 | Piovoso et al. ........................ 364/552 |
| 4,240,110 | 12/1980 | Henry . |
| 4,323,311 | 4/1982 | West et al. ............................. 356/431 |
| 4,367,047 | 1/1983 | Ikin ........................................ 356/431 |
| 4,458,979 | 7/1984 | Röss . |
| 4,490,617 | 12/1984 | Loose . |
| 4,499,383 | 2/1985 | Loose . |
| 4,538,915 | 9/1985 | Faulhaber ............................. 356/431 |
| 4,670,659 | 6/1987 | Loose . |
| 4,714,340 | 12/1987 | Stillwagon ............................... 356/23 |
| 4,737,650 | 4/1988 | West . |
| 4,797,558 | 1/1989 | West . |
| 4,845,356 | 7/1989 | Baker ..................................... 250/225 |
| 4,861,984 | 8/1989 | West . |
| 4,877,323 | 10/1989 | Stillwagon ............................... 356/23 |
| 4,900,153 | 2/1990 | Weber et al. ........................... 356/430 |
| 5,047,640 | 9/1991 | Brunnschweiler et al. . |
| 5,055,679 | 10/1991 | Ninomiya et al. . |
| 5,079,434 | 1/1992 | Weber . |
| 5,168,322 | 12/1992 | Clarke et al. .......................... 356/237 |
| 5,206,700 | 4/1993 | Reynolds et al. ..................... 356/237 |
| 5,225,890 | 7/1993 | Lee et al. ............................... 356/371 |
| 5,243,402 | 9/1993 | Weber et al. .......................... 356/429 |
| 5,274,243 | 12/1993 | Hochgraf . |
| 5,301,129 | 4/1994 | McKaughan et al. ................. 364/552 |
| 5,305,392 | 4/1994 | Longest, Jr. et al. . |
| 5,307,152 | 4/1994 | Boehnlein et al. .................... 356/376 |
| 5,367,378 | 11/1994 | Harding et al. ....................... 356/371 |
| 5,463,429 | 10/1995 | Campbell et al. . |
| 5,566,243 | 10/1996 | Baller et al. . |

*Primary Examiner*—Vincent P. McGraw
*Attorney, Agent, or Firm*—Beyer & Weaver, LLP

[57] ABSTRACT

An illumination system (20) and method for use with an optical web inspection assembly (21) to identify surface defects on a moving material web (25). The illumination system (20) includes an elongated light source (26) having an elongated aperture (46) adapted to transmit a substantially continuous elongated strip of non-collimated light therefrom generally in an entrance direction. An elongated light pipe device (32) is provided having an elongated entrance end (33) and an opposite elongated exit end (36) wherein the entrance end (33) is positioned longitudinally adjacent the light source aperture (46) and configured to substantially receive the strip of light therethrough in the entrance direction. The light pipe (32) includes a smoothly curved interior wall (37) extending from the entrance end (33) to the exit end (36), and defines an optical path configured to reflect and transmit substantially all the light received from the entrance end to the exit end (36). The reflected and transmitted light exit the exit end (36) in a line of illumination (38) generally in an exit direction toward the moving material web (25) such that the intensity of the line of illumination exiting the exit end (36) is substantially equal to the intensity of the strip of light entering the entrance end (33) from the light source (26).

33 Claims, 8 Drawing Sheets

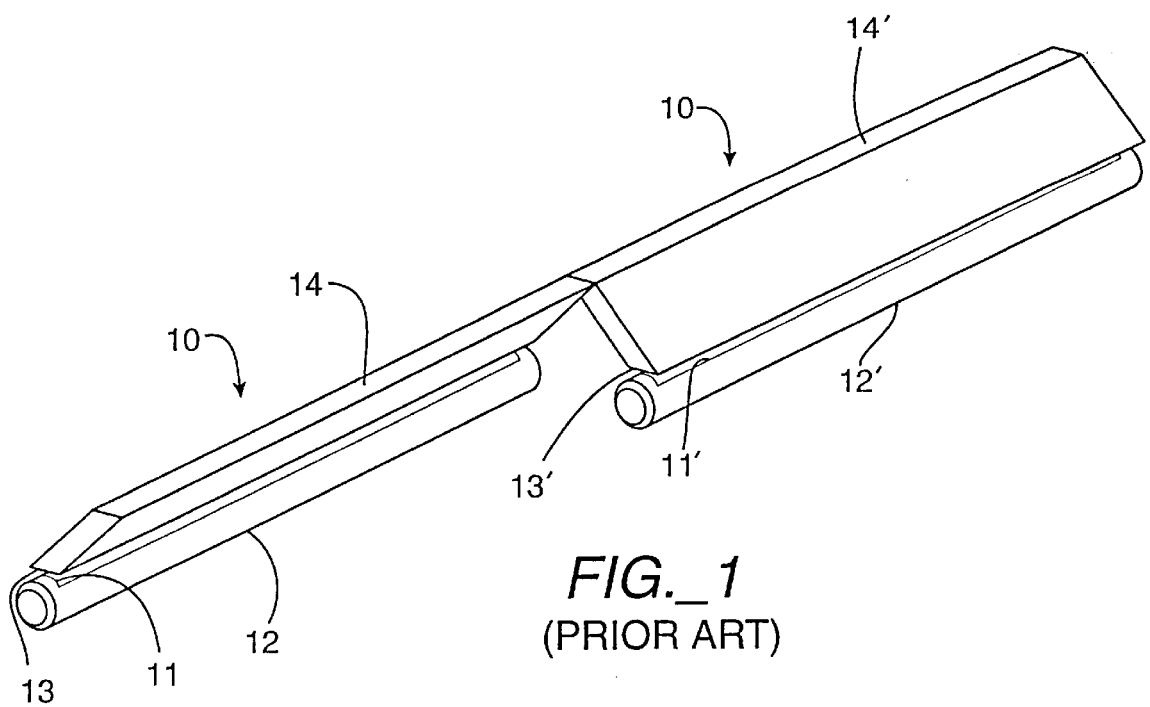
FIG._1
(PRIOR ART)
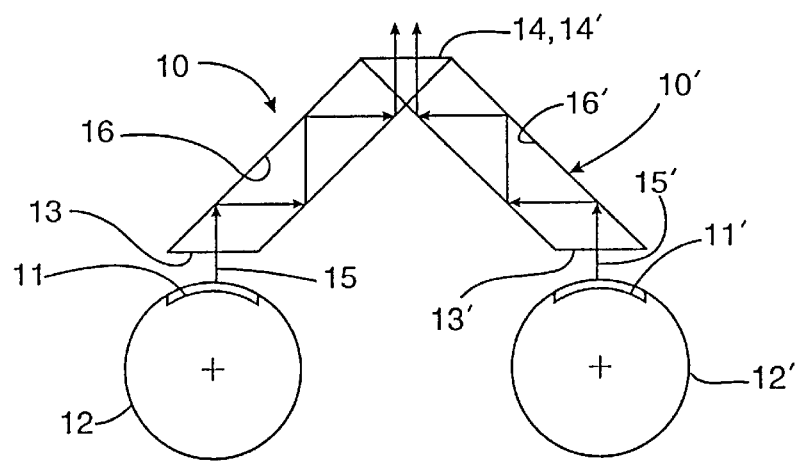
FIG._2
(PRIOR ART)

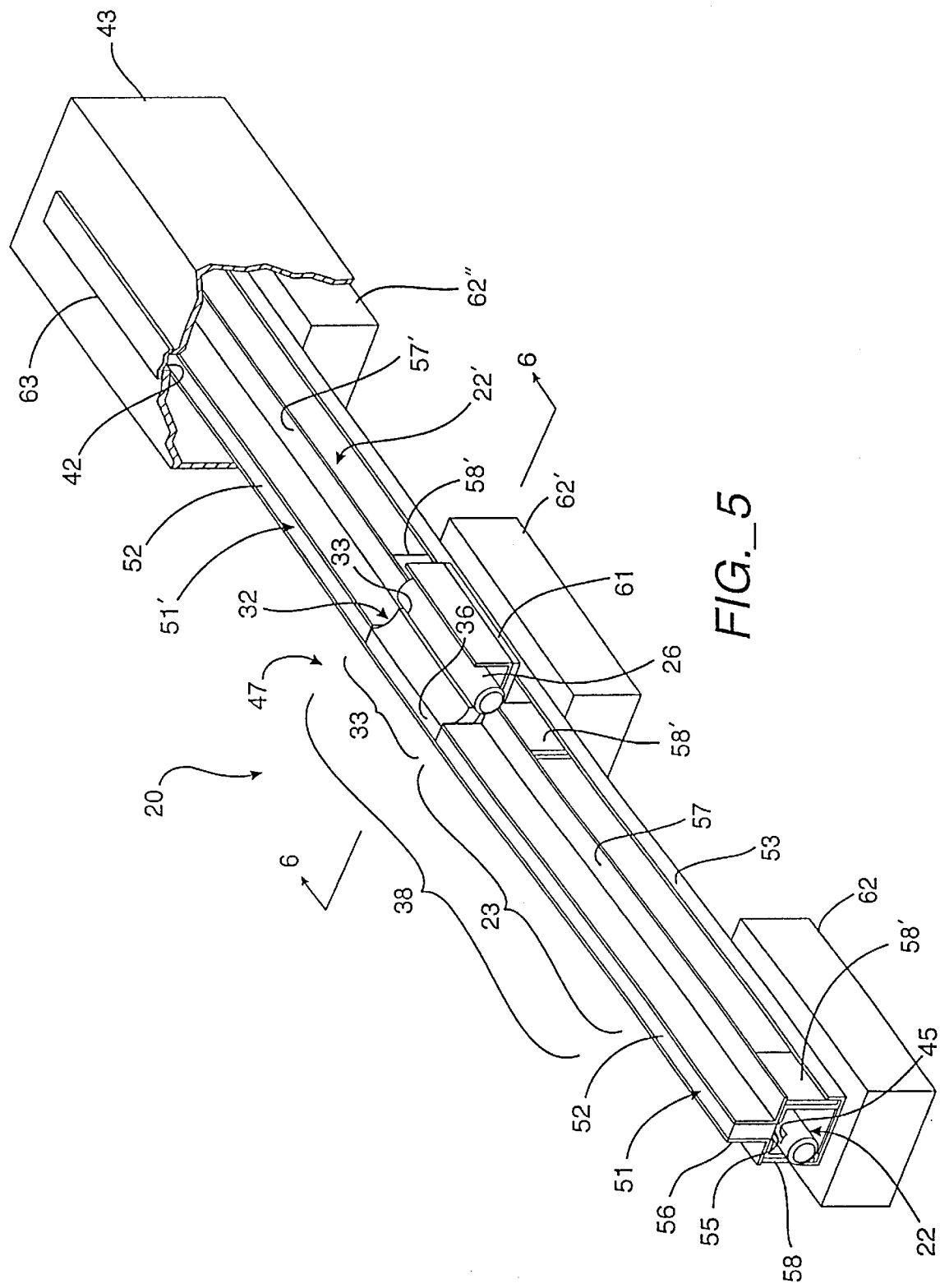
FIG._5

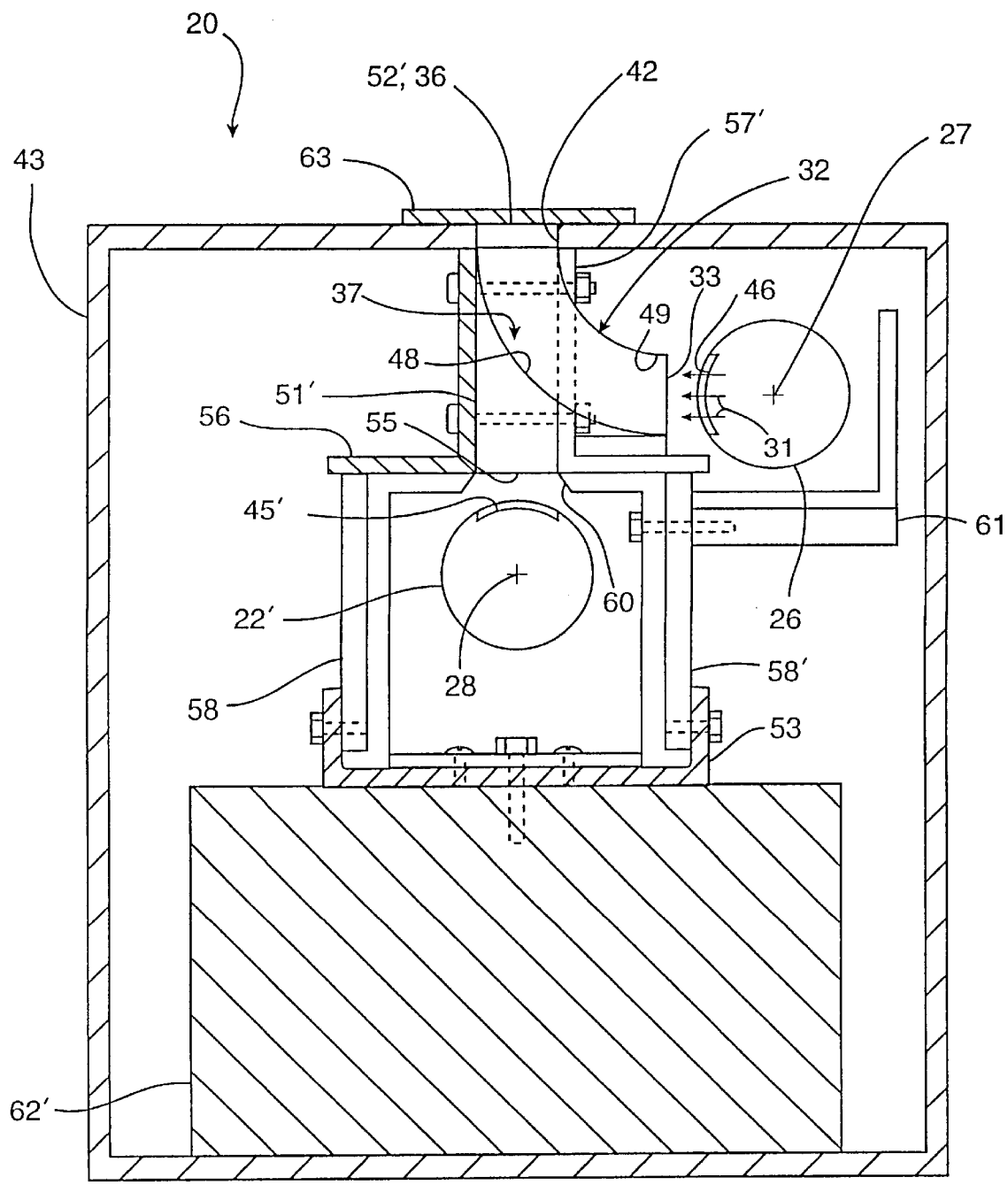
FIG._6

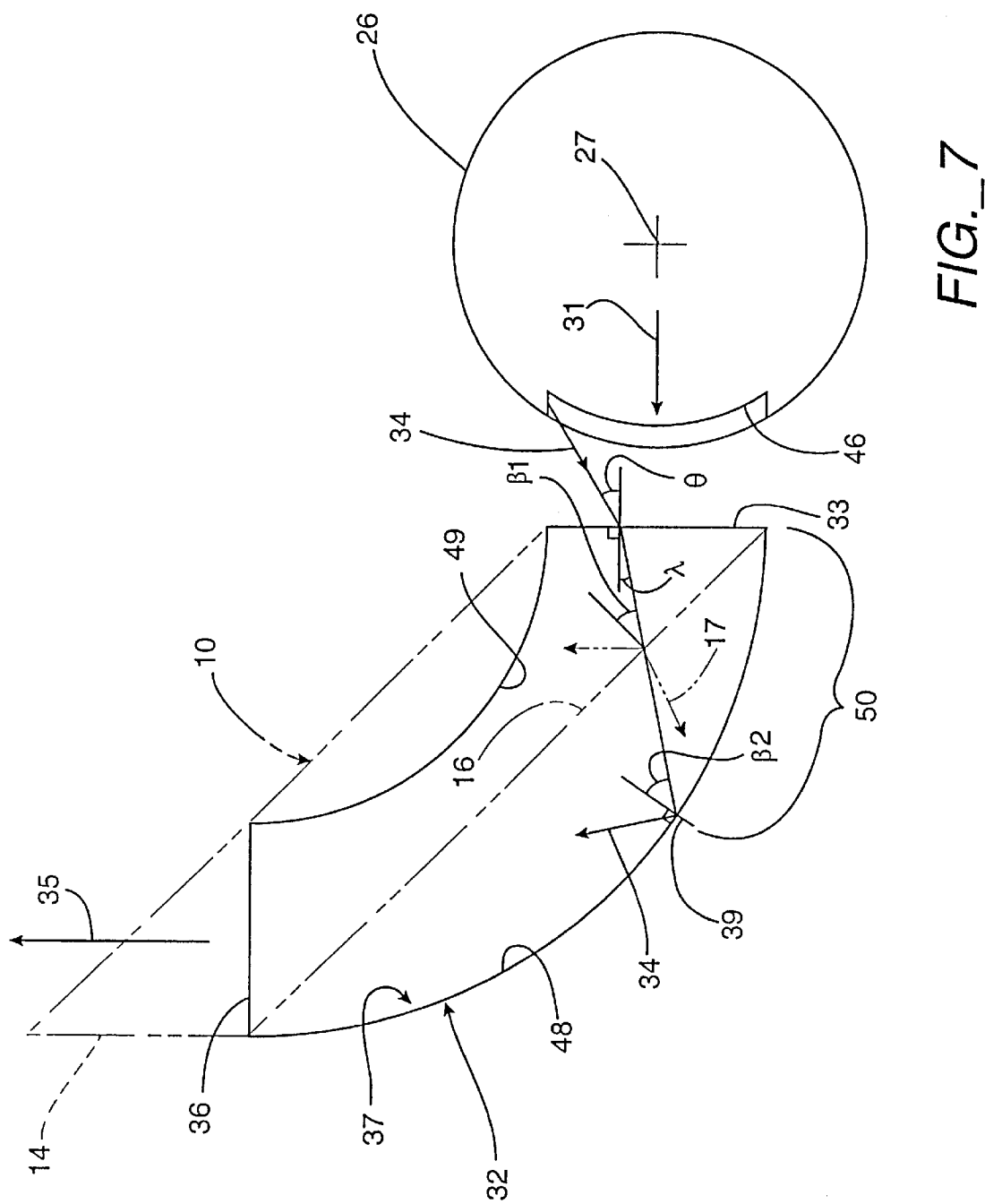
FIG._7

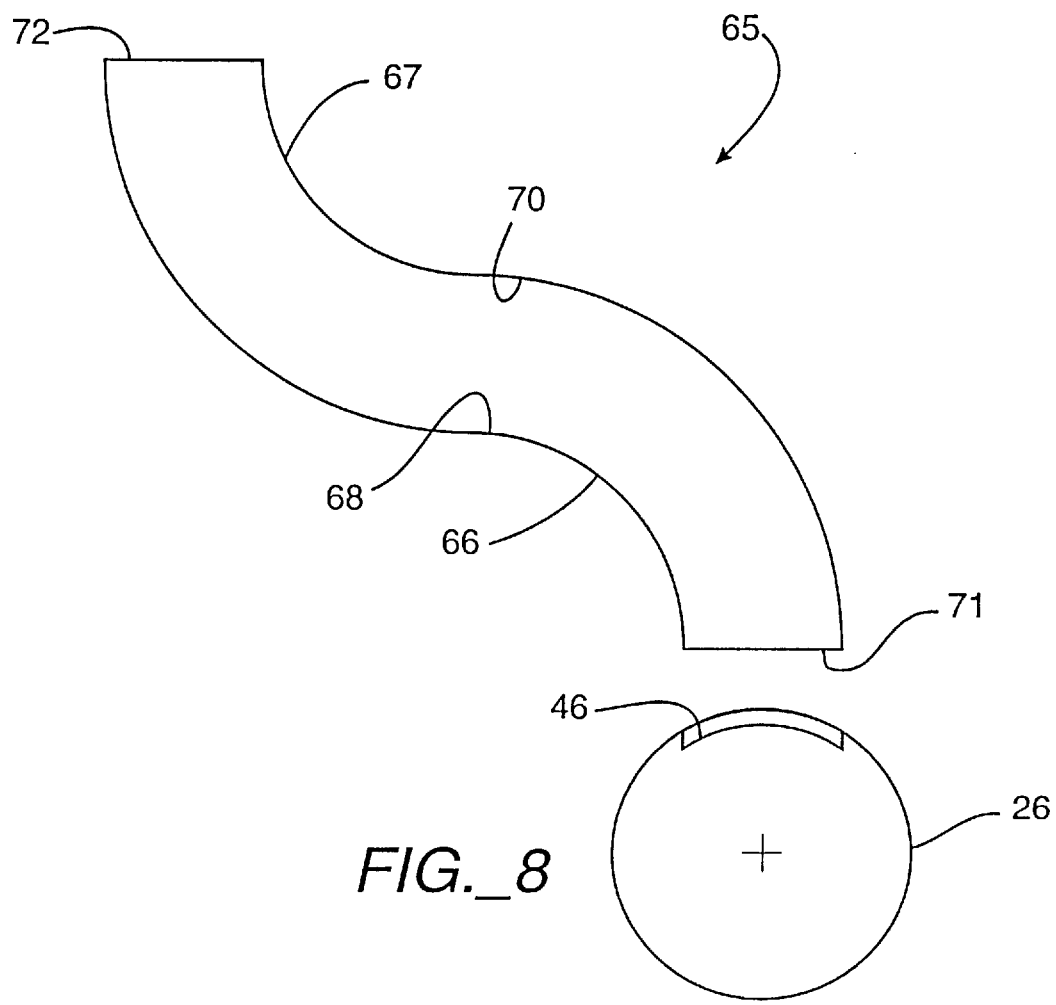
FIG._8

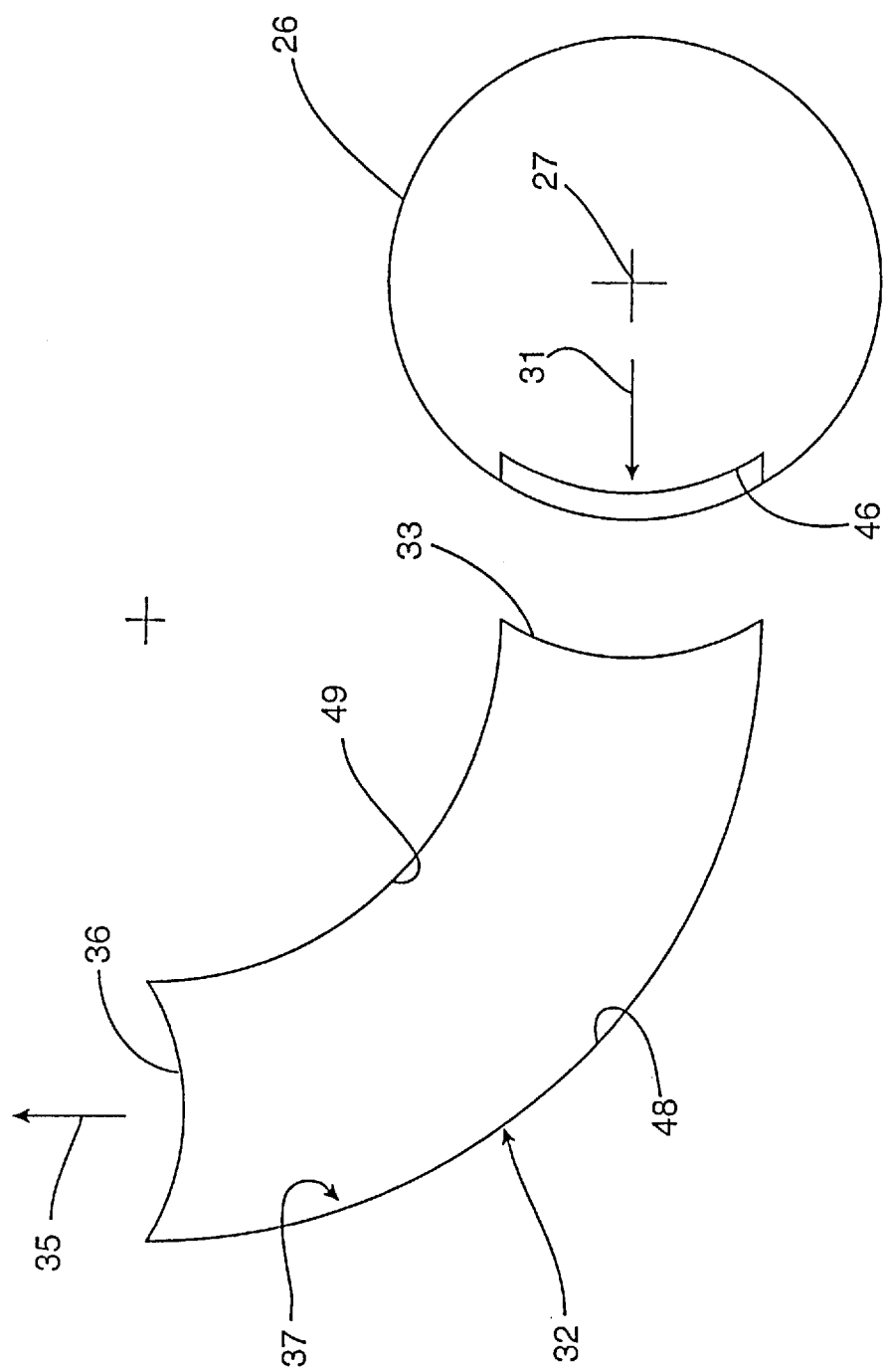
FIG._9

EXPANDABLE, CONTINUOUS ILLUMINATION SOURCE FOR A WEB INSPECTION ASSEMBLY AND METHOD

TECHNICAL FIELD

The present invention relates, generally, to web inspection assemblies and, more particularly, relates to strip light illumination sources for high speed, high resolution web inspection assemblies.

BACKGROUND ART

In recent years, considerable effort has been directed toward on-line web inspection to enhance the uniform quality of material webs, such as paper, glass, plastic, textiles, metallic sheets, fiberglass and sheet substrates. These web inspection assemblies are capable of high speed, high resolution detection and classification of surface imperfections in continuously manufactured products at rates in excess of 1200 feet per minute. Such surface imperfections include tears, through-holes, abrasions and scattering imperfections, impurities preventing local processing, stains and absorbing imperfections, pinch marks, thickness imperfections, and other far side and near side imperfections.

Typically, web inspection assemblies include an illumination source generating a point of light or a strip of light, and a photoelectric light sensor device strategically positioned and angled to receive diffusely reflected light from a target surface illuminated by the generated light. Due to the scattering imperfections on or in the target surface, differences in light intensity of the reflected or transmitted light will be detected which may represent one of the above-mentioned surface imperfections. The light sensor device then delivers a signal to an electronic processing device representative of the type and magnitude of the surface imperfection.

One web inspection system, in particular, employs an electronic line scan camera having a plurality of light sensitive photosites aligned in a linear array in a direction substantially transverse or perpendicular to the travel direction of the moving web (i.e., across the width of the web). In this manner, the entire transverse width of the web can be inspected simultaneously as the web material passes through the target scan line of the camera. Furthermore, while 100% inspection coverage may be achievable regardless of the material web width, this web inspection arrangement advantageously eliminates the need for any moving parts relating to the web scan. In comparison, many prior art web inspection systems for relatively wide width material webs employ rotating or oscillating mirrors to reflect and traverse the light from edge to edge of the traveling web. Typical of these patented assemblies include U.S. Pat. Nos.: 4,323,311; 4,367,047; 4,538,915; 4,737,650 and 4,707,558.

In line scan camera-type web inspection systems, the target surface of the moving material web is then backlit or frontlit with an elongated strip of light radiating from an illumination source which in turn is then reflected into the sight of the scan line of the camera. As the reflected light rays are received by the line scan camera, a lens refracts the light rays onto corresponding photosites. Each photosite generates a signal proportional to the sensed light intensity which collectively form an "image" of the web, which for a line scan device, the "image" is generated by the web motion. The resulting camera output signal, thus, is a video waveform that comprises the sequentially sampled output of all of the photosites.

Since the accuracy, quality and integrity of the web inspection system is largely dependent upon the detection of light intensity variations of the reflected light, it is very important that the strip of light generated from the light source maintain a uniform distribution across the width of the web on the target surface. A non-uniform or fluctuating light distribution may hinder system calibration or result in inconsistent or inaccurate data analysis. Hence, the optimum light source for a web inspection system employing a line scan camera generates a strip or line of light along the line of inspection which is bright, substantially linear and low in power consumption. Another important prerequisite is that the spectrum of light generated by the illumination source should be matched to both the web material and the camera to provide for maximum defect contrast.

Fluorescent lamps, accordingly, are often employed in line scan camera-type web inspection systems to fulfill these prerequisites because of their uniform light distribution, wide spectral light generation, low power consumption and low cost. By placing a linearly extending aperture in the phosphor coating of the bulb, a proper strip of light is generated to impinge the target surface of the web.

While these fluorescent lamp illumination sources are advantageous in many applications, material webs of very large widths pose significant problems. The maximum practical length of the fluorescent lamps, due to cost considerations, is about ten feet. Webs larger than about nine feet, therefore, require at least two fluorescent bulbs situated in an end-to-end manner. Because of the housing and bulb socket constraints of the fluorescent lamps, uniform and continuous lighting along the line of light is prohibited across the width of wide webs since deadband regions occur between the joints of the adjacent the fluorescent lamps. This is due to the fact that the light output and intensity diminishes dramatically about six inches from the ends of the bulb.

One prior art approach was to limit the scan width of the line scan camera to the maximum lamp usable width, and add additional camera and light source components offset in the direction of travel of the material web. This approach adds substantial complexity by increasing the number of cameras and the number signal processing channels. Furthermore, due to the offset, analyzing the shape and location of the imperfection along the web is more problematic.

Another prior art approach, as shown FIGS. 1 and 2, incorporates opposed diagonally extending acrylic light pipes 10 and 10' coupled to the output of the longitudinally extending linear apertures 11, 11 in the adjacent fluorescent lamp bulbs 12, 12'. These light pipes 10, 10' are parallelogram shaped in cross-section and transmit the light from a respective bottom entrance end 13, 13' to a respective top exit end 14, 14' as represented generally by light rays 15, 15' (FIG. 2). The problem with this approach, as shown in FIG. 3, is that a measurable amount of light is lost through the respective side walls 16, 16' of the light pipe when the angle of incidence $\beta$ of refracted incident ray 15 is less than the angle for total internal reflection.

Briefly, for any incident ray passing through two mediums, the general equation for refraction is:

$$\eta_1 \theta_1 = \eta_2 \sin \lambda_2$$

where in this case, $\eta_1 = 1$ for air, and $\eta_2 = 1.5$ for acrylic. Moreover, internal reflection occurs only when $$\sin \beta > 1/\eta_2$$

For acrylic where $\eta_2=1.5$, internal reflection occurs only when $\beta$ is greater than about 41.8°. Depending upon the angle $\alpha$ (FIG. 3) of diagonal side wall 16, a measurable amount of diffuse light 17 radiating from the light source will be transmitted through the side wall 16 when the angle of incident $\beta$ in the acrylic medium is less than 41.8°. Therefore, the light intensity of the strip of remaining light transmitted through the top exit end 14 will be measurably less than the intensity of the light entering the light pipe at the bottom entrance end 13. This loss of intensity has been measured to be up to about 42% (Experiment A below). In fact, to compensate for this intensity loss (as shown in FIGS. 1 and 2), due to the light loss of this light pipe configuration employs two symmetrically opposed light pipes 10, 10' are generally employed with near equal light intensity losses. This tends to balance out the light intensity losses of the two strips of light ultimately exiting the respective light pipe exit end 14, 14', as opposed to providing a more efficient straight vertical light pipe. Accordingly, in the design of FIG. 2, the collective light intensity is measurably reduced.

Another problem associated with this design is that the light intensity across the width of the exit end 14 does not tend to be evenly distributed. Due to the linear configuration of the internal side walls 16, 16', and the general angled entry of the non-collimated diffuse light radiating from the fluorescent light aperture 11, the region of peak transmission or of greatest light intensity for a 30° (from a normal plane) diagonal light pipe is measured to be about 40° to 50° offset from a normal plane longitudinally bisecting the exit end 14. Accordingly, the prior art light pipe design of FIG. 1 is very inefficient from a viewing normal plane longitudinally bisecting the exit end since the mirror image light pipes would each refract the respective peak light intensity about 45° to the opposite sides of that normal plane The collective line of illumination, thus, would not be uniformly distributed from one end to the other end thereof.

While the prior art illumination source devices for line scan cameras have been satisfactory for many web inspection applications, it highly desirable to provide a plurality of linear light sources which collectively generate a uniform, continuous strip of light along the entire material web width.

DISCLOSURE OF INVENTION

Accordingly, it is an object of the present invention to provide an illumination apparatus and method for a web inspection assembly which distributes a continuous, uniform strip of light across the width of the web.

Yet another object of the present invention is to provide an illumination apparatus and method for a web inspection assembly which maximizes the light intensity of light impinging the target surface of a material web from a fluorescent lamp source.

Still another object of the present invention is to provide an illumination source and method for a web inspection assembly which eliminates the deadband region between two end-to-end fluorescent lamps.

Another object of the present invention is to provide an illumination apparatus and method for a web inspection assembly which enable unlimited length extension of the light source.

It is a further object of the present invention is to provide an illumination apparatus and method for a web inspection assembly having a plurality of elongated light sources with independent intensity settings.

Still a further object of the present invention to provide an illumination apparatus for a web inspection assembly which is durable, compact, easy to maintain, has a minimum number of components, cost effective to manufacture, and is easy to use by moderately skilled personnel.

In accordance with the foregoing objects, an illumination system is provided for use with an optical web inspection assembly to identify surface defects on a moving material web. The illumination system includes an elongated light source having an elongated aperture adapted to transmit a substantially continuous elongated strip of non-collimated light therefrom generally in an entrance direction. Further, the illumination system includes an elongated light pipe device having an elongated entrance end and an opposite elongated exit end. The entrance end is positioned longitudinally adjacent the light source aperture and configured to receive the strip of light therethrough in the entrance direction. The light pipe includes a smoothly curved interior wall extending from the entrance end to the exit end, and defines an optical path configured to reflect and transmit substantially all the light received from the entrance end to the exit end. The reflected and transmitted light exit the exit end in a line of illumination generally in an exit direction toward the moving material web such that the intensity of the line of illumination exiting the exit end is substantially equal to the intensity of the strip of light entering the entrance end from the light source.

Preferably, the light pipe is composed of a transparent solid material having an interior wall which includes a first elongated wall smoothly curved inwardly and an opposite second elongated wall extending substantially parallel to the first elongate wall and smoothly curved outwardly about a common longitudinal axis. The first and second elongated walls each have an arc length of about 90° such that the exit direction of the line of illumination exiting the exit end is oriented about 90° from the entrance direction of the elongated strip of light entering the entrance end about the common longitudinal axis.

In another embodiment of the present invention, an illumination system for use with an optical web inspection assembly includes a first elongated light source configured to generate a first elongated strip of light therefrom which impinges the material web substantially continuously from a proximal end to an opposite distal end of the strip of light. An intermediate elongated light source is provided having a longitudinal axis oriented substantially parallel to and off-set from a longitudinal axis of the first elongated light source. The intermediate light source is further adapted to transmit a substantially continuous elongated intermediate strip of light therefrom generally in an entrance direction. The illumination system further includes an elongated light pipe device positioned adjacent to the elongated intermediate light source and having an elongated entrance end and an opposite elongated exit end. The entrance end is configured to receive the second strip of light in the entrance direction. The light pipe further includes an interior wall between the entrance end and the exit end configured to reflect and transmit substantially all the second strip of light from the entrance end to the exit end. The light, thus, exits therefrom generally in an exit direction toward the moving material web and in substantially an end-to-end manner with the distal end of the first strip of light such that a collective substantially linear, continuous and uniformly distributed line of illumination is formed on the surface of the material web.

Additionally, a method of illuminating a moving material web is also comprising the steps of: (A) emitting a substantially continuous elongated strip of light from a light source in an entrance direction; and (B) receiving the strip of light in an elongated entrance end of an elongated light pipe. The method further includes the step of (C) reflecting the strip of light, traveling in the entrance direction, in the light pipe off of smoothly curved interior walls extending from the entrance end to an elongated exit end. The curved walls define an optical path configured to reflect and transmit substantially all the light received from the entrance end to the exit end for exit therefrom in a line of illumination generally in an exit direction toward the moving material web. The intensity of the line of illumination exiting the exit end is substantially equal to the intensity of the strip of light entering the entrance end from the light source. The method illuminating the moving material web of the present invention; finally, includes the step of (D) illuminating the moving web with the line of illumination transmitted from the exit end of the light pipe.

BRIEF DESCRIPTION OF THE DRAWING

The assembly of the present invention has other objects and features of advantage which will be more readily apparent from the following description of the best mode of carrying out the invention and the appended claims, when taken in conjunction with the accompanying drawing, in which:

FIG. 1 is a top perspective view of a prior art illumination system employing two symmetric diagonal light pipe devices.

FIG. 2 is an enlarged side elevation view of the prior art light pipe device of FIG. 1.

FIG. 5 is an enlarged, top perspective view, partially broken-away, of the illumination system of FIG. 4.

FIG. 6 is an enlarged side elevation view, in cross-section, of the illumination system taken substantially along the plane of line 6—6 in FIG. 5.

FIG. 7 is an enlarged side elevation view, in cross-section, of the illumination system of FIG. 6 illustrating the reflection of the light rays passing through the light pipe.

FIG. 8 is an enlarged side elevation view, in cross-section, of the an alternative embodiment the light pipe device of the present invention.

FIG. 9 is an enlarged side elevation view, in cross-section, of an alternative embodiment of the illumination system of FIG. 6.

BEST MODE OF CARRYING OUT THE INVENTION

Figure 3:
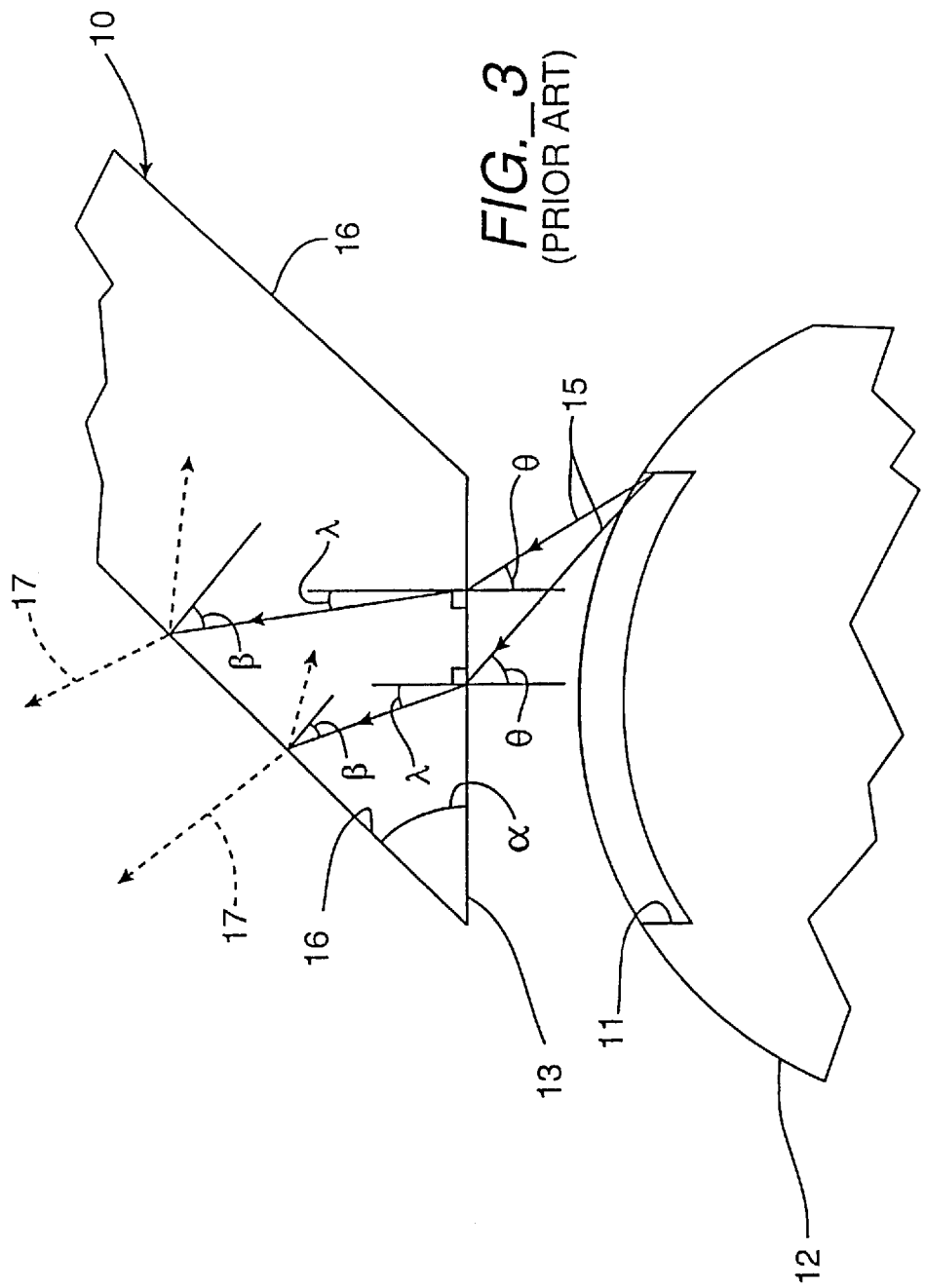
FIG. 3 is an enlarged schematic side view of the prior art light pipe device of FIG. 2 illustrating an incident ray.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Attention is now directed to FIGS. 4–7 where an illumination system, generally designated 20, of the present invention is illustrated for use with an optical web inspection assembly 21. Briefly, illumination system 20 includes a first or primary elongated light source 22 configured to generate a first elongated strip of light 23 therefrom which impinges the material web 25 substantially continuously from a proximal end to an opposite distal end of the strip of light 23. An intermediate elongated light source, generally designated 26, is provided having a longitudinal axis 27 oriented substantially parallel to and off-set from a longitudinal axis 28 of the first elongated light source 22. The intermediate light source 26 is further adapted to transmit a substantially continuous, non-collimated, elongated intermediate strip of light therefrom generally in an entrance direction (represented by arrow 31 in FIG. 7). The illumination system 20 further includes an elongated light pipe device, generally designated 32, positioned adjacent to the elongated intermediate light source 26 and having an elongated entrance end 33 and an opposite elongated exit end 36. The entrance end 33 is configured to receive the second strip of light in the entrance direction. The light pipe further includes an interior wall 37 between the entrance end 33 and the exit end 36 which is configured to reflect and transmit substantially all the second strip of light from the entrance end to the exit end. The second strip of light, thus, exits therefrom generally in an exit direction (represented by arrow 35 in FIG. 7) toward the moving material web 25 and in substantially an end-to-end manner with the distal end of the first strip of light 23 such that a collective substantially linear, continuous and uniformly distributed line of illumination 38 is transmitted therefrom to impinge the surface of the material web 25.

Accordingly, an illumination system is provided which creates a continuous and uniformly distributed strip of light to illuminate a relatively wide material web (i.e., generally greater than about 9 feet) for web inspection. This strip of light is generated through a plurality of individual elongated strips of light aligned in an end-to-end arrangement. The present invention illumination system thus is capable of forming an unlimited length line of illumination by effectively providing nearly a seamless light joint between the adjacent light sources. Moreover, due to the current design of the curved interior walls of the present invention, the intensity of the light exiting the exit end is substantially the same as the intensity of the light entering the entrance end since light loss caused by transmission through the interior walls of the light pipe is substantially reduced. Finally, the curved interior walls uniformly disperse and distribute of the light across the light pipe width.

Figure 4:
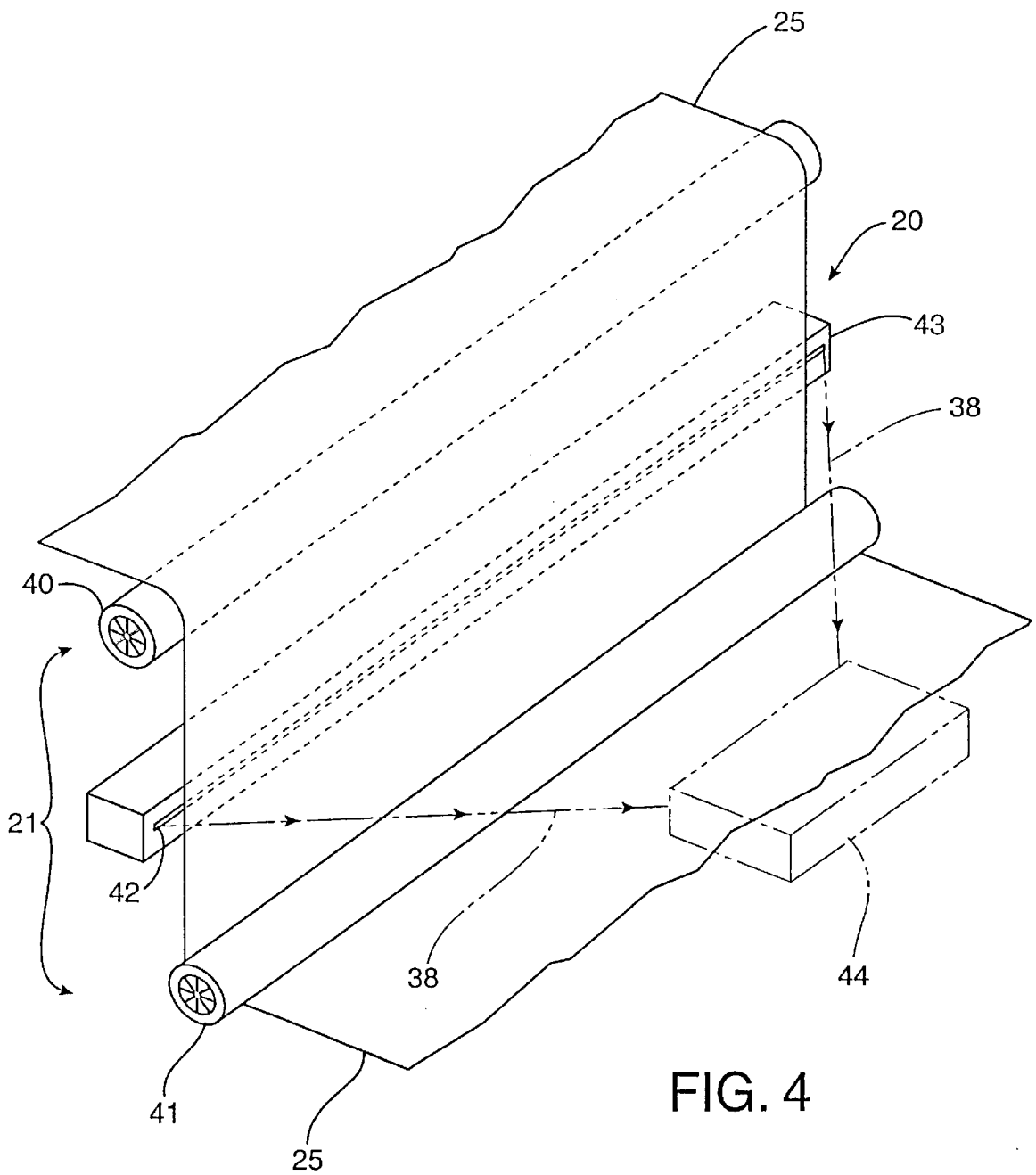
FIG. 4 is a top perspective view of an illumination system constructed in accordance with the present invention cooperating with a web inspection system for inspection of the material web.

Referring now to FIG. 4, the illumination system 20 is illustrated operably mounted to a web assembly 21. Briefly, the material web 25 is shown being advanced longitudinally along spaced rollers 40 and 41. A bright, uniformly distributed, collective, line of light 38 is emitted from an elongated slit 42 provided in housing assembly 43 of illumination system 20. In this embodiment, the material web is inspected through backlighting where a collective line of illumination 38 is transmitted transversely through the material web 25, as opposed to a reflected light inspection assembly employed for more opaque material webs. It will be appreciated, however, that in the latter arrangement, the illumination system 20 would be positioned on the same side of the material web 25 as camera 44, and angled with respect to the material web to reflect light into the camera lens.

In either embodiment, a conventional linear Charge Coupled Device (CCD) array or camera 44 is positioned to receive the transmitted or reflected light (shown in phantom lines in FIG. 4). Housed in the CCD or camera 44 is a plurality of photosites aligned in a linear array (not shown) to detect the light intensity of the reflected light. Each photosite, in turn, generates an electronic signal representative of the sensed intensity of light which collectively form an image of the web. The signals are processed by a computer (not shown), which stores a record of the video waveform that comprises the sequentially sampled output of all of the photosites.

In the preferred embodiment and as best illustrated in FIG. 5, intermediate light source 26 is positioned between, and offset from, two co-axially aligned, elongated primary light sources 22, 22' oriented end-to-end. This may be better viewed in FIG. 6 where the longitudinal axis 27 of intermediate light source 26 is illustrated offset from and parallel to the longitudinal axes 28 of the primary light sources 22, 22'. While the offset distance between the longitudinal axes may vary, it will be understood that the distance therebetween is at least one light bulb diameter.

Briefly, conventional elongated fluorescent lamps (primary light sources 22, 22' and intermediate light source 26) are employed, each of which produces a straight, unbroken, uniform strip of light. Each bulb includes an elongated slit or aperture 45, 45' and 46 etched in their phosphor coating. These linear apertures 45, 46 enable non-collimated strips of lights to be directionally emitted from the light source, for example, in the direction of the elongated entrance end 33, represented by arrow 31 in FIG. 7. Typical of these fluorescent light sources is the VHO fluorescent aperture-type lamp with a thirty degree (30°) aperture.

Due to the light source housing and socket assemblies, which are not shown for clarity, the light source aperture 45, 45' of the primary light sources 22, 22' begins about three (3) to about six (6) inches from the end of the housing. Accordingly, when the fluorescent lamps are positioned end-to-end to increase the length of the strip of light, a deadband region 47 is typically created between the joints of the primary light sources. In this deadband region, typically about ten (10) to fourteen (14) inches in length, light intensity is considerably reduced and thus cannot be utilized for web inspection purposes without additional lighting in this region.

To receive and transmit a substantial portion of the emitted light from the intermediate light source, the length and width dimension of the intermediate light pipe entrance end 33 (FIGS. 5 and 7) is preferably at least as large as the corresponding length and width of the intermediate light source aperture 46. Light capture is further facilitated by positioning the entrance end 33 adjacent and parallel to the light source aperture 46 at a distance of about ⅛ to 1 inch, and more preferably about ¼ inch therefrom.

As above-mentioned, the intermediate illumination system 20 maintains a uniform distribution of light 38 across the length thereof by providing and positioning an optimally curved light pipe 32 in the deadband region 47 between the two end to end primary light sources 22, 22'. This design is advantageous in that for an offset light pipe design, the light intensity loss caused by the undesirable transmission of light through the side walls of the curved light pipe is substantially minimized.

FIGS. 5–7 best illustrate that intermediate light pipe 32 is preferably in the shape of a quarter-cylindrical shell having an elongated entrance end 33 and an elongated exit end 36. Briefly, as will be described in greater detail below, the transparent light pipe 32 is preferably provided by polished plastic, preferably solid acrylic or the like, which may be formed through extrusion techniques, casting or machining. The intermediate light pipe 32 includes a smoothly curved interior wall 37 extending from the entrance end 33 to the exit end 36 which forms an optical path configured to internally reflect and transmit substantially all the light 38 received in the entrance end toward the exit end.

In the preferred embodiment, the interior wall 37 primarily includes an elongated first wall 48 smoothly curved inwardly and an opposite elongated second wall 49 smoothly curved outwardly toward the first inwardly curved wall. These opposed, curved interior walls 48, 49 are co-axial and concentric about longitudinal axis 27 so as to generally conform with one another. In the embodiment illustrated in FIGS. 5–7, the vertically oriented entrance end 33 and the horizontally situated exit end 36 are preferably rectangular in shape and are oriented about 90° relative one another about longitudinal axis 27. Preferably, the outer radius (R) is about 1 to 3 inches, and more preferably about 1-¾ inches, while the inner radius (r) is about 1 to 2 inches, and more preferably about 1-¼ inch. It will be appreciated that depending upon the application, the diameters and respective lengths of the arc segments may vary without departing from the true nature and spirit of the present invention.

In accordance with the present invention, the smooth inwardly curved first wall 48 and the smooth outwardly curved second wall 49 cooperate to internally reflect substantially all the directionally diffused light (i.e., emitted through linear aperture 46 and entering entrance end 33) toward the exit end 36 for transmission in the exit direction (represented by arrow 35 in FIG. 7). This is primarily due to the optimal curvature of the inwardly curved first wall 48 which is configured to internally reflect an incident ray inwardly until it is emitted from the exit end 36. Directly comparing the curved light pipe with the prior art diagonal light pipes (phantom lines in FIG. 7), the angular range of fully internally reflected incident rays 34 is greater for the curved light pipe than for the prior art diagonal light pipe. This is especially prominent at lower region 50 of curved first wall 48 closest to the entrance end 33. For example, as shown in FIG. 7, the light rays 34 emanating from an upper portion of the light source 26 through linear aperture 46 and toward the lower portion 50 of the inwardly curved first wall 48 will generally be transmitted (transmitted ray 17) through side wall 16 of the prior art diagonal light pipe (FIG. 1). However, for the curved light pipe 32, light rays 34 traveling along identical paths will contact the inwardly curved first wall 48 at a reduced angle, relative a normal plane 39 intersecting the first wall 48, enabling an increased chance of internal reflection back into the light pipe. In essence, for the same light ray 34, angle β2 for curved light pipe 32 is greater than angle β1 for diagonal light pipe 10 which increases the chance of internal reflection. This results in substantially all the directional, diffused light entering the bottom entrance end 33 from linear aperture 46 to be internally reflected from the side walls 48, 49 and transmitted through to exit end 36. Collectively, a greater amount of light is directed toward the exit end 36, resulting in a more efficient light pipe.

As mentioned above, for solid acrylic plastic having an index of refraction ($\eta_{LP}$) of about 1.5, full internal reflection occurs only when β is greater than about 41.8°. Therefore, only incident rays directed toward the interior walls at incident angles less than 41.8° will be transmitted through the interior walls. As set forth below in Experiment A, the intermediate curved light pipe 32 is capable of reflecting and refracting at least about 82% of the light entering entrance end 33 toward and out of exit end 36. This respective transmission efficiency is substantially similar to the light transmission efficiency of a straight light pipe. In contrast, the diagonal light pipe 10 typically transmits about 48% of the incoming light from the exit end.

Therefore, the intermediate curved light pipe 32 can be effectively employed in the deadband region 47 between two end-to-end oriented vertical or straight light pipes 51, 51' without experiencing a significant disparity in light intensity between the exit ends 52, 52' and 36 of the primary straight light pipes 51, 51', and the intermediate curved light pipe 32. Accordingly, the light intensity of the illumination system may be maximized. In comparison, the prior art diagonal light pipes of FIGS. 1 and 2 were less efficient and may not be employed with the more light intensity efficient vertical or straight light pipes since too large of an imbalance across the collective light strip length would result.

Moreover, the dispersion characteristics of the curved light pipe 32 are more advantageous than the diagonal light pipe design since the peak transmission or greatest intensity light exiting the light pipe is normal to exit end 36 enabling a more uniform distribution of light not only across the length but across the width of the intermediate light pipe 32 as well. Due to the smooth curvature of the inward interior walls 48, 49, the offset, light intensive "hot spots" are eliminated across the exit end width (FIGS. 6 and 7).

As indicated, the primary light source 22 (only one of which will be described for clarity) is preferably provided by a fluorescent lamp having an elongated slit or aperture 45 etched in the phosphor coating to enable a diffuse strip of light to be emitted therefrom. The length of the primary fluorescent lamps are typically up to about eight (8) feet in length as compared to the twenty-four (24) to thirty-six (36) inch length of the intermediate lamps 26. Conventional electrical sockets (not shown for clarity) are included at the opposed ends of the primary light source 22 which provide both electrical connection and vertical support for the light source. These sockets are coupled to a U-shaped support bracket 53 which extends from one end of the illumination system 20 to the other end thereof.

In accordance with the present invention, an efficient, straight light pipe 51 is employed to transmit the strip of light toward the material web 25. The transparent primary light pipe 51 is composed of polished plastic, preferably acrylic, having a cross-sectional dimension of about ½ inch by about 1-⅝ inch. Similar to the curved intermediate light pipe 32, the primary light pipe entrance end 55 preferably conforms (i.e., in length and width) to the primary light source aperture 45, and is positioned adjacent thereto about ⅛ inch from the primary light source.

As best viewed in FIGS. 5 and 6, the two primary light pipes 51, 51' are mounted between two opposed L-shaped brackets 56, 57 and 57'. The rear L-shaped bracket 56 preferably extends the full longitudinal length of the line of illumination, which further facilitates aligned support along the backside of the light pipes during assembly and operation. The front spaced L-shaped brackets 57, 57' extend along the frontside longitudinal length of the respective primary light pipe 22, 22' and cooperate with the rear bracket 56 for alignment of the light pipes therebetween.

To supportably retain the primary light pipes 51, 51' relative the primary light sources 22, 22' of the illumination system 20, a plurality of pairs of spaced-apart suspension brackets 58, 58' (FIGS. 5 and 6) are mounted to U-shaped support bracket 53 in a longitudinally spaced manner. These suspension brackets provide vertical support for the L-shaped brackets 56, 57 and 56, 57' which in turn are rigidly coupled to the primary light pipes 51, 51'. The respective light pipes, thus, can be supported and aligned a predetermined distance from the respective primary light sources.

A longitudinal groove 60 is formed between the spaced-apart brackets 58, 58' (FIG. 6) which enable the transmission of the strip of light 23 from the primary light source aperture 45 to the bottom entrance end 55 of the primary light pipe 51. This spacing between the brackets 58, 58' further enables air to flow around the primary light sources for cooling purposes.

Similar to the primary fluorescent lamps, the intermediate fluorescent lamp 26 is vertically supported and electrically connected through a pair of opposed electrical sockets (not shown for clarity) coupled to the ends of the intermediate lamp. The intermediate electrical sockets are mounted to a horizontal shaped support bracket 61 coupled to and spanning the distance from the side walls of the front suspension brackets 58. Collectively, the suspension brackets and L-shaped brackets cooperate to align the light pipes in an end-to-end linear relationship, and align the respective fluorescent lamp relative the respective light pipe entrance end.

In accordance with the present invention, fluorescent lamps 22 and 22' and fluorescent lamp 26 includes a respective individual high frequency electronic ballast 62, 62' and 62" electrically coupled thereto. These ballasts, such as a MERCRON™ ballast, enable individual regulation of the power source for each light source so that the light intensity or brightness of the respective fluorescent can be precisely and incrementally adjusted relative one another. Once the setting of each ballast is manually or automatically adjusted, an even more uniform distribution of light across the length of the light strip may be achieved. Preferably, the primary lamps 22 and 22' share a common ballast, while secondary lamp 26 is coupled to an individual ballast.

During line voltage fluctuations or due to light source aging or the like, the light intensity of the individual lamp may fluctuate or deteriorate in intensity over time. Individual light sensors (not shown), such as a photoresistor, are thus preferably provided at the respective apertures of the lamps or at the exit ends of the light pipes to monitor the light intensity outputs thereof. This photo sensor provides a feedback or servo signal which electronically communicates with the respective light source and ballast so that the average light intensity can be maintained about an arbitrary setpoint. A nominal average intensity can therefore be maintained at the adjusted, preset level as the lamp ages.

Illumination system 20 further includes a housing assembly 43 enclosing the primary fluorescent lamps 22, 22' and the intermediate fluorescent lamp 26 from the surrounding environment. As best viewed in FIGS. 5 and 6, housing assembly 43 is provided by a rectangular casing having an elongated slot 42 aligned with the exit ends 52, 52' and 36 of the corresponding light pipes for transmission of the collective strip of light 38 therethrough. For environments having an abundance of debris or the like, the housing assembly 43 can be configured to form an airtight or hermetic seal to prevent debris contamination. A transparent polycarbonate window 63 is provided extending over elongated slot 42 to further facilitate debris isolation.

At least one fan apparatus (not shown) communicates with housing assembly 43 to cool the fluorescent lamp and light pipe components. Such cooling improves the efficiency of the fluorescent lamp output. Preferably, two fans are provided each positioned proximate opposed ends of the housing to generate air flow from one end to the other end thereof.

Referring now to FIG. 8, an alternative embodiment of the curved light pipe is illustrated having an S-shaped profile essentially comprised of a first elbow portion 66 and a second opposed elbow portion 67. Similar to the curved light pipe 32 of FIG. 6, cooperation between the opposed interior walls 68, 70 substantially reflects all the directionally diffused light from the entrance end 33 toward the exit end 36. This is primarily due to the optimal curvature of the curved first wall 68 and the opposed second curved wall 70 which are configured to internally reflect the incident rays inwardly until it is emitted from the exit end 72.

In this embodiment, the direction of the diffused light entering entrance end 71 and exiting exit end 72 are substantially similar. It will be appreciated, however, that the relative angled orientations of the entrance end and the exit end are inconsequential as long as the interior walls are optimally curved to internally reflect the incoming light rays.

In yet another alternative embodiment of the present invention (FIG. 9), the entrance end 33 is inwardly curved transversely along a width thereof from one end of the light pipe 32 to the opposite end thereof. Preferably, in this embodiment, curved to generally conform to the aperture 46 of fluorescent lamp 26. This enables any light pipe (not just curved light pipe 32) to be positioned slightly closer to the lamp aperture while maintaining the necessary proper cooling of the lamp entrance end. Moreover, due to the geometry of the entrance end 33, light collection in the light pipe is more efficient.

As further viewed in FIG. 9, the exit end 36 may also be inwardly curved transversely along a width thereof from one end of the light pipe 32 to the opposite end thereof. Such a curvature has the effect of reducing the divergence of the emitted light in a narrower band width than the actual width of the light pipe exit end. Accordingly, the intensity of the emitted strip of light may be increased relative the width. Depending upon the radius of curvature of the exit end, this arrangement would require the material web to be positioned at the focal point of the curvature.

In another aspect and as apparent from the description of the present invention, a method is provided for illuminating a moving material web 25 comprising the steps of: (A) emitting a substantially continuous elongated strip of light from a light source 26 in an entrance direction (arrow 31 in FIG. 7); and (B) receiving the strip of light in an elongated entrance end 33 of an elongated light pipe 32. The method further includes the step of (C) reflecting the strip of light, traveling in the entrance direction, in the light pipe 32 off of smoothly curved interior walls 48, 49 extending from the entrance end 33 to an elongated exit end 36. The curved walls 48, 49 define an optical path configured to reflect and transmit substantially all the light received from the entrance end 33 to the exit end 36 for exit therefrom in a line of illumination generally in an exit direction (arrow 35 in FIG. 7) toward the moving material web 25. The intensity of the line of illumination exiting the exit end is substantially equal to the intensity of the strip of light entering the entrance end 33 from the light source 26. The method illuminating the moving material web 25 of the present invention, finally, includes the step of (D) illuminating the moving web 25 with the line of illumination 38 transmitted from the exit end 36 of the light pipe 32.

The following experiment serves to more fully describe the benefits of the above-described invention, as well as to set forth the best mode contemplated for carrying out various aspects of the invention. It is to be understood that the specific embodiment of the curved light pipe employed in this experiment in no way serves to limit the true scope of the invention, but rather is presented for experimental purposes.

EXPERIMENT A

An experiment was conducted to compare the light transmission characteristics between a straight light pipe, a diagonal light pipe and the curved light pipe of the present invention. Each light pipe was constructed from solid, transparent acrylic polished on all sides and having the same dimensions at the entrance ends and the exit ends. The straight, rectangular light pipe measured ½×1-⅝×10 inches; while the diagonal light pipe was fabricated to a 30° from normal light pipe measuring ½×1.67×10 inches. The quarter-cylindrical shell light pipe had an arc length of about 80° and measured ½×1.67×10 inches.

The fluorescent lamp employed was a 48" VHO fluorescent aperture-type lamp having a 30° aperture. The width of a chord drawn across the aperture at the surface of the lamp envelope was approximately 0.40". The detector was a calibrated Silicon photo diode, having a spectral response typical of unfiltered Si sensors, which were part of a Newport Optical Power Meter, Model 815. The detector was 1.0 $cm^2$ in area mounted behind a translucent diffuser. The clear aperture was 0.450" D. This detector was connected to an amplifier/readout device by shielded cable, and had a threaded ND 03 filter mounted to attenuate the input level. The instrument was calibrated to read incident power in mill-watts.

Measurements were made at several locations along the length of the lamp aperture and along the exit ends of the respective light pipes. The data listed in TABLE A represents the percent transmission measured directly at the exit end of the light pipe relative the light intensity of the lamp which was measured at the aperture. Each value represents the mean of three to five discrete data points taken in succession over different points along the length of the lamp or light pipe exit end. This technique was performed to average out any adverse effects which may have been caused due to optical quality of the lens surface.

TABLE A

| Fluorescent Lamp | Straight Light Pipe | Diagonal Light Pipe | Curved Light Pipe |
| --- | --- | --- | --- |
| 100% (9.39 mW) | 84% | 48% | 82.5% |

As provided in TABLE A, the transmission percent value of the transmitted light through the straight light pipe and the curved light pipe are substantially equivalent. Accordingly, it is feasible to combine the straight light pipe and the curved light pipe to increase the collective length of the line of illumination without compromising continuity and uniformity of the light intensity across the length. In fact, the light intensity of the collective, continuous, uniformly distributed line of illumination may be maximized since the disparity between the transmitted light of the two light pipes is very small. Minor adjustments to the individual ballasts will nearly eliminate any light intensity disparity.

In contrast, the transmission percent value of the transmitted light through the diagonal light pipe is comparatively very poor. The substantial loss of light through the side walls of the diagonal light pipe causes too great a disparity between the straight light pipe and the diagnonal light pipe to ever practically consider such a combination. The overall light intensity of this design, hence, is substantially inferior.

What is claimed is:

1. An illumination system for use with an optical web inspection assembly to identify surface defects on a moving material web, said illumination system comprising:

an elongated light source having an elongated aperture adapted to transmit a substantially continuous elongated strip of non-collimated light therefrom generally in an entrance direction; and an elongated light pipe device having an elongated entrance end and an opposite elongated exit end, said entrance end being positioned longitudinally adjacent the light source aperture and configured to receive said strip of light therethrough in said entrance direction, said light pipe having a smoothly curved interior wall portion between the entrance end and the exit end and defining an optical path configured to reflect and transmit substantially all the light received from said entrance end to said exit end for exit therefrom in a line of illumination generally in an exit direction toward the moving material web such that the intensity of said line of illumination exiting the exit end is substantially equal to the intensity of said strip of light entering the entrance end from said light source.

2. The illumination system as defined in claim 1 wherein, said interior wall portion includes a first elongated wall smoothly curved inwardly and an opposite second elongated wall substantially parallel said first elongate wall and smoothly curved outwardly.

3. The illumination system as defined in claim 2 wherein, said first and second elongated walls are quarter-cylindrical shell shaped each having a radius of curvature originating from a common longitudinal axis.

4. The illumination system as defined in claim 3 wherein, said first and second elongated walls each have an arc length of about 90° such that said exit direction of the line of illumination exiting the exit end is about 90° rotated about the common longitudinal axis from said entrance direction of the elongated strip of light entering the entrance end.

5. The illumination system as defined in claim 4 wherein, the radius of curvature of the first elongated wall is about 1-¾ inches, and the radius of curvature of the second elongated wall is about 1-¼ inches.

6. The illumination system as defined in claim 1 wherein, said exit direction of the line of illumination exiting said light pipe at the exit end is at about a 90° angle from said entrance direction of the strip of light entering said light pipe at the entrance end.

7. The illumination system as defined in claim 1 wherein, said light pipe is composed of a transparent plastic.

8. The illumination system as defined in claim 1 wherein, said interior wall portion is generally S-shaped such that the exit direction of the line of illumination exiting said light pipe at the exit end is substantially parallel to said entrance direction of the strip of light entering said light pipe at the entrance end.

9. The illumination system as defined in claim 1 wherein, said elongated light source is a fluorescent lamp.

10. The illumination system as defined in claim 1 wherein, said entrance end is inwardly curved transversely along a width thereof from one end of the light pipe to the opposite end thereof.

11. The illumination system as defined in claim 10 wherein, the inward curve of the entrance end substantially conforms to the outward curvature of the elongated aperture of the elongated light source.

12. The illumination system as defined in claim 11 wherein, said exit end is inwardly curved transversely along a width thereof from one end of the light pipe to the opposite end thereof.

13. The illumination system as defined in claim 10 wherein, said entrance end is generally shaped as a sector of a cylindrical shell.

14. The illumination system as defined in claim 1 wherein, said exit end is inwardly curved transversely along a width thereof from one end of the light pipe to the opposite end thereof.

15. The illumination system as defined in claim 1 wherein, said entrance end is generally rectangular shaped.

16. The illumination system as defined in claim 15 wherein, said exit end is generally rectangular shaped.

17. An illumination system for use with an optical web inspection assembly to identify surface defects on a moving material web, said illumination system comprising:

an elongated first light source configured to generate a substantially continuously, non-collimated first elongated strip of light therefrom generally in an exit direction to impinge the material web;

an elongated intermediate light source having a longitudinal axis offset from a longitudinal axis of the first light source, and adapted to generate a substantially continuous, non-collimated intermediate elongated strip of light therefrom generally in an entrance direction; and an elongated curved light pipe device positioned adjacent to said intermediate light source and having an elongated entrance end and an opposite elongated exit end, said entrance end being configured to substantially receive the intermediate strip of light of the intermediate light source generated in the entrance direction, said light pipe having a smoothly curved interior wall portion between the entrance end and the exit end configured to reflect and transmit substantially all said intermediate strip of light collected in said entrance end for transmission through said exit end generally in the exit direction, and in substantially an end-to-end aligned manner where a proximal end of a reflected intermediate strip of light is substantially linearly aligned with a distal end of the first strip of light such that the first strip of light and the reflected intermediate strip of light collectively form a substantially linear, continuous and uniformly distributed line of illumination on a surface of the material web.

18. The illumination system as defined in claim 17 wherein, said interior wall portion includes a first elongated wall smoothly curved inwardly and an opposite second elongated wall substantially parallel said first elongate wall and smoothly curved outwardly.

19. The illumination system as defined in claim 18 wherein, said first and second elongated walls are quarter-cylindrical shell shaped each having a radius of curvature originating from a common longitudinal axis.

20. The illumination system as defined in claim 19 wherein, said first and second elongated walls each have an arc length of about 90° such that said exit direction of the line of illumination exiting the exit end is about 90° rotated about the common longitudinal axis from said entrance direction of the elongated strip of light entering the entrance end.

21. The illumination system as defined in claim 17 further including:

an elongated second light source configured to generate a substantially continuously, non-collimated third elongated strip of light therefrom generally in the exit direction, and in substantially an end-to-end aligned manner with the reflected intermediate strip of light where a proximal end of the second strip of light is substantially linearly aligned with a distal end of the reflected second strip of light such that the first strip of light, the reflected intermediate strip of light and the second strip of light collectively form a substantially linear, continuous and uniformly distributed line of illumination on a surface of the material web.

22. The illumination system as defined in claim 21 wherein, a longitudinal axis of the second light source is co-axially aligned with the longitudinal axis of the first light source.

23. The illumination system as defined in claim 22 further including:

a first straight light pipe device having an elongated first entrance end and an opposite elongated first exit end, said first entrance end being positioned longitudinally adjacent the first light source and configured to substantially receive said first strip of light therethrough generally in said exit direction, and said first exit end aligned with and substantially co-linear with the intermediate exit end of the intermediate light pipe, and a second straight light pipe device having an elongated second entrance end and an opposite elongated second exit end, said second entrance end being positioned longitudinally adjacent the second light source and configured to substantially receive said second strip of light therethrough generally in said exit direction, and said second exit end aligned with and substantially co-linear with the intermediate exit end of the intermediate light pipe.

24. The illumination system as defined in claim 23 wherein, said first light source includes an elongated first aperture adapted to transmit said first elongated strip of light therefrom generally in the exit direction, said intermediate light source includes an elongated intermediate aperture adapted to transmit said intermediate elongated strip of light therefrom generally in the entrance direction, and said second light source includes an elongated second aperture adapted to transmit said third elongated strip of light therefrom generally in the exit direction.

25. The illumination system as defined in claim 24 further including:

a regulating device coupled between the first light source, the second light source and the intermediate light source to regulate the power to each light source to incrementally adjust the light intensity therebetween.

26. The illumination system as defined in claim 25 wherein, said regulating device includes:
a first ballast device operatively coupled to the first light source for independent incremental adjustment of the power to the first light source;

a second ballast device operatively coupled to the second light source for independent incremental adjustment of the power to the second light source; and an intermediate ballast device operatively coupled to the intermediate light source for independent incremental adjustment of the power to the intermediate light source.

27. The illumination system as defined in claim 26 wherein, said regulating device further includes:
a first light sensor responsive to the light intensity of the first strip of light emitted from the first light source, and in response, generating a first feedback signal electrically communicating with the first ballast device;

a second light sensor responsive to the light intensity of the second strip of light emitted from the second light source, and in response, generating a second feedback signal electrically communicating with the second ballast device; and an intermediate light sensor responsive to the light intensity of the intermediate strip of light emitted from the intermediate light source, and in response, generating an intermediate feedback signal electrically communicating with the intermediate ballast device.

28. The illumination system as defined in claim 17 further including:

a first straight light pipe device having an elongated first entrance end and an opposite elongated first exit end, said first entrance end being positioned longitudinally adjacent the first light source and configured to substantially receive said first strip of light therethrough generally in said exit direction, and said first exit end aligned with and substantially co-linear with the intermediate exit end of the intermediate light pipe.

29. The illumination system as defined in claim 28 wherein, said first light source includes an elongated first aperture adapted to transmit said first elongated strip of light therefrom generally in the exit direction, and said intermediate light source includes an elongated intermediate aperture adapted to transmit said intermediate elongated strip of light therefrom generally in the entrance direction.

30. The illumination system as defined in claim 28 further including:

a regulating device coupled between the first light source and the intermediate light source to regulate the power to each light source to incrementally adjust the light intensity therebetween.

31. The illumination system as defined in claim 32 wherein, said regulating device includes:
a first ballast device operatively coupled to the first light source for independent incremental adjustment of the power to the first light source; and an intermediate ballast device operatively coupled to the intermediate light source for independent incremental adjustment of the power to the intermediate light source.

32. The illumination system as defined in claim 31 wherein, said regulating device further includes:
a first light sensor responsive to the light intensity of the first strip of light emitted from the first light source, and in response, generating a first feedback signal electrically communicating with the first ballast device; and an intermediate light sensor responsive to the light intensity of the intermediate strip of light emitted from the intermediate light source, and in response, generating an intermediate feedback signal electrically communicating with the intermediate ballast device.

33. A method of illuminating a moving material web for use with an optical web inspection assembly to identify surface defects comprising the steps of:

emitting a substantially continuous elongated strip of light from a light source in an entrance direction;

receiving said strip of light in an elongated entrance end of an elongated light pipe;

reflecting said strip of light, traveling in the entrance direction, in said light pipe off of smoothly curved interior wall portion between the entrance end and an elongated exit end and defining an optical path configured to reflect and transmit substantially all the light received from said entrance end to said exit end for exit therefrom in a line of illumination generally in an exit direction toward the moving material web such that the intensity of said line of illumination exiting the exit end is substantially equal to the intensity of said strip of light entering the entrance end from said light source; and illuminating the moving web with the line of illumination transmitted from said exit end of the light pipe.

* * * * *